United States Patent
Seth et al.

(10) Patent No.: US 11,116,843 B2
(45) Date of Patent: Sep. 14, 2021

(54) CONJUGATED ANTISENSE COMPOUNDS AND THEIR USE

(71) Applicant: Ionis Pharmaceuticals, Inc., Carlsbad, CA (US)

(72) Inventors: Punit P. Seth, Carlsbad, CA (US); Michael Oestergaard, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/761,786

(22) PCT Filed: Sep. 26, 2016

(86) PCT No.: PCT/US2016/053836
§ 371 (c)(1),
(2) Date: Mar. 20, 2018

(87) PCT Pub. No.: WO2017/053999
PCT Pub. Date: Mar. 30, 2017

(65) Prior Publication Data
US 2018/0256729 A1    Sep. 13, 2018

Related U.S. Application Data

(60) Provisional application No. 62/233,292, filed on Sep. 25, 2015.

(51) Int. Cl.
| | | |
|---|---|---|
| *A61K 47/55* | (2017.01) | |
| *A61K 47/54* | (2017.01) | |
| *A61K 9/00* | (2006.01) | |
| *A61K 31/7105* | (2006.01) | |
| *C12N 15/11* | (2006.01) | |
| *C12N 15/113* | (2010.01) | |

(52) U.S. Cl.
CPC .......... *A61K 47/551* (2017.08); *A61K 9/0019* (2013.01); *A61K 31/7105* (2013.01); *A61K 47/549* (2017.08); *A61K 47/554* (2017.08); *C12N 15/111* (2013.01); *C12N 15/1135* (2013.01); *C12N 15/1137* (2013.01); *C12N 2310/14* (2013.01); *C12N 2310/315* (2013.01); *C12N 2310/3231* (2013.01); *C12N 2310/3341* (2013.01); *C12N 2310/3515* (2013.01); *C12Y 207/11001* (2013.01)

(58) Field of Classification Search
CPC .... A61K 38/00; A61K 38/16; C07K 2319/00; C12N 9/22; C12N 9/6424
USPC ... 435/6.1, 69.1, 91.1, 91.31, 325, 455, 458; 514/44; 536/23.1, 23.2, 24.5
See application file for complete search history.

(56) References Cited

U.S. PATENT DOCUMENTS

| | | |
|---|---|---|
| 2004/0110296 A1 | 6/2004 | Vargeese et al. |
| 2007/0161591 A1 | 7/2007 | Aronin et al. |
| 2010/0048676 A1 | 2/2010 | Chang |
| 2010/0222417 A1 | 9/2010 | Zimmermann et al. |
| 2011/0319475 A1 | 12/2011 | Collard et al. |
| 2014/0045919 A1* | 2/2014 | Manoharan ............ A61K 47/55 514/44 A |
| 2014/0107180 A1 | 4/2014 | Macleod et al. |
| 2017/0190778 A1* | 7/2017 | Layne ................ C07K 16/2863 |
| 2019/0062743 A1* | 2/2019 | Uhlmann ............. C12N 15/113 |
| 2020/0354751 A1* | 11/2020 | Zhang ..................... C12N 9/22 |

FOREIGN PATENT DOCUMENTS

| | | |
|---|---|---|
| WO | WO 2017/053995 | 3/1917 |
| WO | 2012012443 A2 | 1/2012 |
| WO | WO 2013/089283 | 6/2013 |
| WO | WO 2014/132671 | 9/2014 |
| WO | WO 2014/179620 | 11/2014 |
| WO | WO 2014/192310 | 12/2014 |
| WO | WO 2014/203518 | 12/2014 |
| WO | 2015021457 A2 | 2/2015 |

OTHER PUBLICATIONS

International Search Report for PCT/US16/053836 dated Dec. 28, 2016.
Koppel et al., "Tissue-specific and neural activity-regulated expression of human BDNF gene in BAC transgenic mice" BMC Neuroscience (2009) 10: 1-14.
Extended EP Search Report for 16849895.4 dated May 3, 2019.

* cited by examiner

*Primary Examiner* — Jane J Zara
(74) *Attorney, Agent, or Firm* — McNeil Baur PLLC

(57) ABSTRACT

The present disclosure provides duplexes comprising a first oligomeric compound and a second oligomeric compound wherein the second oligomeric compound comprises a conjugate group. In certain embodiments, the duplex modulates the amount or activity of a target nucleic acid in extra hepatic tissues and/or extra hepatic cells. In certain embodiments, the duplex modulates the amount or activity of a target nucleic acid in hepatic tissues and/or hepatic cells.

16 Claims, No Drawings
Specification includes a Sequence Listing.

CONJUGATED ANTISENSE COMPOUNDS AND THEIR USE

SEQUENCE LISTING

The present application is being filed along with a Sequence Listing in electronic format. The Sequence Listing is provided as a file entitled CORE0137USASEQ_ST25.txt, created on Mar. 20, 2018, which is 8 Kb in size. The information in the electronic format of the sequence listing is incorporated herein by reference in its entirety.

FIELD

The present disclosure provides duplexes comprising a first oligomeric compound and a second oligomeric compound wherein the second oligomeric compound comprises a conjugate group. In certain embodiments, the duplex modulates the amount or activity of a target nucleic acid in extra hepatic tissues and/or extra hepatic cells. In certain embodiments, the duplex modulates the amount or activity of a target nucleic acid in hepatic tissues and/or hepatic cells.

BACKGROUND

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of diseases.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients. For another example, an antisense oligonucleotide targeting ApoB, KYNAMRO™, has been approved by the U.S. Food and Drug Administration (FDA) as an adjunct treatment to lipid-lowering medications and diet to reduce low density lipoprotein-cholesterol (LDL-C), ApoB, total cholesterol (TC), and non-high density lipoprotein-cholesterol (non HDL-C) in patients with homozygous familial hypercholesterolemia (HoFH).

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy. Traditionally, antisense compounds, including modified oligonucleotides, have deomonstrated good functional uptake into liver tissue. However, there is still a need to facilitate uptake and distribution of antisense compounds into other cell types.

SUMMARY OF THE INVENTION

After an oligomeric compound is administered to a subject, different organs, tissues, and cells receive different amounts of the oligomeric compound. The distribution of the oligomeric compound to different organs, tissues, and cells depends on many factors. For example, the degree to which a given oligomeric compound binds to plasma proteins may affect the distribution of a given oligomeric compound to various tissues. In certain embodiments, the degree to which a given oligomeric compound is recognized by certain cell-surface receptors may affect the distribution of a given oligomeric compound to various tissues or cells.

Oligomeric compounds typically show good distribution to the liver after administration to a subject. However, in certain embodiments a need exists to deliver oligomeric compounds to other tissues within a subject. For example, a need exists to deliver oligomeric compounds to one or more extra-hepatic tissues such as adipose tissue or muscle tissue. In certain embodiments, the present disclosure provides oligomeric compounds comprising a modified oligonucleotide and a conjugate group, wherein the conjugate group enhances delivery of the modified oligonucleotide to one or more extra-hepatic tissues.

In certain embodiments, the present disclosure provides a duplex comprising a first oligomeric compound and a second oligomeric compound, wherein the second oligomeric compound comprises a modified oligonucleotide and a conjugate group. In certain embodiments, the duplex modulates the amount or activity of a target nucleic acid transcript in an extra-hepatic cell to a greater extent than a duplex having a second oligomeric compound that does not comprise a conjugate.

The present disclosure provides the following non-limiting numbered embodiments:

Embodiment 1

A duplex comprising a first oligomeric compound and a second oligomeric compound wherein the first oligomeric compound comprises a first modified oligonucleotide consisting of 10-30 linked nucleosides and has a nucleobase sequence complementary to the nucleobase sequence of the second oligomeric compound and to an extra-hepatic nucleic acid target; and the second oligomeric compound comprises a second modified oligonucleotide consisting of 10-30 linked nucleosides and a conjugate group;

wherein the conjugate group comprises a conjugate moiety and a conjugate linker, wherein the conjugate moiety is selected from among: a lipid, vitamin, steroid, $C_5$-$C_{30}$ saturated alkyl group, $C_5$-$C_{30}$ unsaturated alkyl group, fatty acid, and lipophilic group; and wherein the conjugate linker comprises at least one cleavable moiety.

Embodiment 2

A duplex comprising a first oligomeric compound and a second oligomeric compound wherein the first oligomeric compound comprises a first modified oligonucleotide consisting of 10-30 linked nucleosides and has a nucleobase sequence complementary to the nucleobase sequence of the second oligomeric compound and to an extra-hepatic nucleic acid target or a hepatic nucleic acid target; and the second oligomeric compound comprises a second modified oligonucleotide consisting of 10-30 linked nucleosides and a conjugate group;

wherein the modified oligonucleotide has a sugar motif other than:

1-4 2'-OMethyl-modified nucleosides at the 5'-end;

10-15 central nucleosides each comprising an unmodified RNA sugar moiety; and 1-4 2'-OMethyl-modified nucleosides at the 3'-end;

wherein the conjugate group comprises a conjugate moiety and a conjugate linker, wherein the conjugate moiety is selected from among: a lipid, vitamin, steroid, $C_5$-$C_{30}$ saturated alkyl group, $C_5$-$C_{30}$ unsaturated alkyl group, fatty acid, and lipophilic group; and wherein the conjugate linker comprises at least one cleavable moiety.

Embodiment 3

A duplex comprising a first oligomeric compound and a second oligomeric compound wherein the first oligomeric compound comprises a first modified oligonucleotide consisting of 10-30 linked nucleosides and has a nucleobase sequence complementary to the nucleobase sequence of the second oligomeric compound and to an extra-hepatic nucleic acid target or a hepatic nucleic acid target; and the second oligomeric compound comprises a second modified oligonucleotide consisting of 10-30 linked nucleosides and a conjugate group;

wherein the conjugate group comprises a conjugate moiety and a conjugate linker, wherein the conjugate moiety is selected from among: a lipid, steroid, $C_5$-$C_{30}$ saturated alkyl group, $C_5$-$C_{30}$ unsaturated alkyl group, fatty acid, and a lipophilic group other than a vitamin; and wherein the conjugate linker comprises at least one cleavable moiety.

Embodiment 4

The duplex of any of embodiments 1-3, wherein the extra-hepatic nucleic acid target is not expressed in the liver at a significant level.

Embodiment 5

The duplex of any of embodiments 1-3, wherein the extra-hepatic nucleic acid target is expressed in the liver at a significant level.

Embodiment 6

The duplex of any of embodiments 1-5, wherein the extra-hepatic nucleic acid target is expressed in at least one extra-hepatic cell type selected from among: white fat cells, brown fat cells, adipocytes, macrophages, cancer cells, tumor cells, smooth muscle cells, lymphocytes, heart muscle cells, and pulmonary cells.

Embodiment 7

The duplex of any of embodiments 1-6, wherein the extra-hepatic nucleic acid target is expressed in at least two extra-hepatic cell types.

Embodiment 8

The duplex of any of embodiments 1-7, wherein the extra-hepatic nucleic acid target is expressed in at least three extra-hepatic cell types.

Embodiment 9

The duplex of any of embodiments 1-8, wherein the extra-hepatic nucleic acid target is expressed in at least four extra-hepatic cell types.

Embodiment 10

The duplex of any of embodiments 1-9, wherein the extra-hepatic nucleic acid target is expressed in white fat cells.

Embodiment 11

The duplex of any of embodiments 1-10, wherein the extra-hepatic nucleic acid target is expressed in brown fat cells.

Embodiment 12

The duplex of any of embodiments 1-11, wherein the extra-hepatic nucleic acid target is expressed in adipocytes.

Embodiment 13

The duplex of any of embodiments 1-12, wherein the extra-hepatic nucleic acid target is expressed in macrophages.

Embodiment 14

The duplex of any of embodiments 1-13, wherein the extra-hepatic nucleic acid target is expressed in cancer cells.

Embodiment 15

The duplex of any of embodiments 1-14, wherein the extra-hepatic nucleic acid target is expressed in tumor cells.

Embodiment 16

The duplex of any of embodiments 1-15, wherein the extra-hepatic nucleic acid target is expressed in smooth muscle cells.

Embodiment 17

The duplex of any of embodiments 1-16, wherein the extra-hepatic nucleic acid target is expressed in heart muscle cells.

Embodiment 18

The duplex of any of embodiments 1-17, wherein the extra-hepatic nucleic acid target is expressed in lymphocytes.

Embodiment 19

The duplex of any of embodiments 1-18, wherein the extra-hepatic nucleic acid target is expressed in at least one extra-hepatic tissue selected from among: skeletal muscle, cardiac muscle, smooth muscle, adipose, white adipose, brown adipose, spleen, bone, intestine, adrenal, testes, ovary, pancreas, pituitary, prostate, skin, uterus, bladder, brain, glomerulus, distal tubular epithelium, breast, lung, heart, kidney, ganglion, frontal cortex, spinal cord, trigeminal ganglia, sciatic nerve, dorsal root ganglion, epididymal fat, diaphragm, and colon.

Embodiment 20

The duplex of any of embodiments 1-19, wherein the extra-hepatic nucleic acid target is expressed in at least two extra-hepatic tissues.

Embodiment 21

The duplex of any of embodiments 1-20, wherein the extra-hepatic nucleic acid target is expressed in at least three extra-hepatic tissues.

Embodiment 22

The duplex of any of embodiments 1-21, wherein the extra-hepatic nucleic acid target is expressed in at least four extra-hepatic tissues.

Embodiment 23

The duplex of any of embodiments 1-22, wherein the extra-hepatic nucleic acid target is expressed in skeletal muscle.

Embodiment 24

The duplex of any of embodiments 1-23, wherein the extra-hepatic nucleic acid target is expressed in cardiac muscle.

Embodiment 25

The duplex of any of embodiments 1-24, wherein the extra-hepatic nucleic acid target is expressed in smooth muscle.

Embodiment 26

The duplex of any of embodiments 1-25, wherein the extra-hepatic nucleic acid target is expressed in epididymal fat.

Embodiment 27

The duplex of any of embodiments 1-26, wherein the extra-hepatic nucleic acid target is expressed in white adipose tissue.

Embodiment 28

The duplex of any of embodiments 1-27, wherein the extra-hepatic nucleic acid target is expressed in the spleen.

Embodiment 29

The duplex of any of embodiments 1-28, wherein the extra-hepatic nucleic acid target is expressed in bone.

Embodiment 30

The duplex of any of embodiments 1-29, wherein the extra-hepatic nucleic acid target is expressed in bone marrow.

Embodiment 31

The duplex of any of embodiments 1-30, wherein the extra-hepatic nucleic acid target is expressed in the intestine.

Embodiment 32

The duplex of any of embodiments 1-31, wherein the extra-hepatic nucleic acid target is expressed in adrenal tissue.

Embodiment 33

The duplex of any of embodiments 1-32, wherein the extra-hepatic nucleic acid target is expressed in the testes.

Embodiment 34

The duplex of any of embodiments 1-33, wherein the extra-hepatic nucleic acid target is expressed in the ovaries.

Embodiment 35

The duplex of any of embodiments 1-34, wherein the extra-hepatic nucleic acid target is expressed in the pancreas.

Embodiment 36

The duplex of any of embodiments 1-35, wherein the extra-hepatic nucleic acid target is expressed in the pituitary.

Embodiment 37

The duplex of any of embodiments 1-36, wherein the extra-hepatic nucleic acid target is expressed in the prostate.

Embodiment 38

The duplex of any of embodiments 1-37, wherein the extra-hepatic nucleic acid target is expressed in the skin.

Embodiment 39

The duplex of any of embodiments 1-38, wherein the extra-hepatic nucleic acid target is expressed in the uterus.

Embodiment 40

The duplex of any of embodiments 1-39, wherein the extra-hepatic nucleic acid target is expressed in the bladder.

Embodiment 41

The duplex of any of embodiments 1-40, wherein the extra-hepatic nucleic acid target is expressed in the brain.

Embodiment 42

The duplex of any of embodiments 1-41, wherein the extra-hepatic nucleic acid target is expressed in the glomerulus.

Embodiment 43

The duplex of any of embodiments 1-42, wherein the extra-hepatic nucleic acid target is expressed in the distal tubular epithelium.

Embodiment 44

The duplex of any of embodiments 1-43, wherein the extra-hepatic nucleic acid target is expressed in the breast.

Embodiment 45

The duplex of any of embodiments 1-44, wherein the extra-hepatic nucleic acid target is expressed in the lung.

Embodiment 46

The duplex of any of embodiments 1-45, wherein the extra-hepatic nucleic acid target is expressed in the heart.

Embodiment 47

The duplex of any of embodiments 1-46, wherein the extra-hepatic nucleic acid target is expressed in the kidney.

Embodiment 48

The duplex of any of embodiments 1-47, wherein the extra-hepatic nucleic acid target is expressed in the colon.

Embodiment 49

The duplex of any of embodiments 1-48, wherein the extra-hepatic nucleic acid target is expressed in the ganglion.

Embodiment 50

The duplex of any of embodiments 1-49, wherein the extra-hepatic nucleic acid target is expressed in the frontal cortex.

Embodiment 51

The duplex of any of embodiments 1-50, wherein the extra-hepatic nucleic acid target is expressed in the spinal cord.

Embodiment 52

The duplex of any of embodiments 1-51, wherein the extra-hepatic nucleic acid target is expressed in the trigeminal ganglia.

Embodiment 53

The duplex of any of embodiments 1-52, wherein the extra-hepatic nucleic acid target is expressed in the sciatic nerve.

Embodiment 54

The duplex of any of embodiments 1-53, wherein the extra-hepatic nucleic acid target is expressed in the dorsal root ganglion.

Embodiment 55

The duplex of any of embodiments 1-54, wherein the extra-hepatic nucleic acid target is an endogenous RNA transcript.

Embodiment 56

The duplex of embodiment 55, wherein the RNA transcript is a pre-mRNA.

Embodiment 57

The duplex of embodiment 55, wherein the RNA transcript is an mRNA.

Embodiment 58

The duplex of embodiment 55, wherein the RNA transcript is a toxic RNA.

Embodiment 59

The duplex of embodiment 55, wherein the RNA transcript is a non-coding RNA.

Embodiment 60

The duplex of embodiment 55, wherein the RNA transcript is a microRNA.

Embodiment 61

The duplex of any of embodiments 1-54, wherein the extra-hepatic nucleic acid target is viral nucleic acid.

Embodiment 62

The duplex of any of embodiments 1-58, wherein the extra-hepatic nucleic acid target is selected from among: ATGL, CD40, TNF-α, CD36, DMPK, DNM2, DMD, DUX4, LMNA, ZFN9, SGLT2, and GCCR.

Embodiment 63

The duplex of any of embodiments 1-58, wherein the extra-hepatic nucleic acid target is selected from among: Androgen Receptor (AR), ANGPTL3, DGAT2, eIF4E, Factor XI, FGFR4, GCCR, GCGR, GHR, PTP1B, SMRT, STAT3, Them1, TRPV4, FTO, MC4R, TMEM18, KCTD15, GNPDA2, SH2B1, MTCH2, NEGR1, BDNF, ETV5, Leptin, leptin receptor, FAIM2, KCNMA1, MAF, NRXN3, TFAP2B, MSRA, AGPAT2, BSCL2, AKT2, PPARγ, LMNA, ZMPSTE24, DGAT1, TNFα, IL-6, Resistin, PAI-1, TBC1D1, METAP2, VEGF, AIF-1, JNK1, CB1, RIP140, TIF2, ANGPT1, ANGPT2, EIF4EBP2, CDK5, SLC13A5, Perilipin 1, Perilipin 2, Perilipin 3, Perilipin 4, HGF, GDF3, TNKs, KATNA1, ChREBP, ATF4, BASP-1, NNMT.

Embodiment 64

The duplex of any of embodiments 1-61, wherein the extra-hepatic nucleic acid target is other than any of: Androgen Receptor (AR), ANGPTL3, DGAT2, eIF4E, Factor XI, FGFR4, GCCR, GCGR, GHR, PTP1B, SMRT, STAT3, Them1, TRPV4, FTO, MC4R, TMEM18, KCTD15, GNPDA2, SH2B1, MTCH2, NEGR1, BDNF, ETV5, Leptin, leptin receptor, FAIM2, KCNMA1, MAF, NRXN3, TFAP2B, MSRA, AGPAT2, BSCL2, AKT2, PPARγ, LMNA, ZMPSTE24, DGAT1, TNFα, IL-6, Resistin, PAI-1, TBC1D1, METAP2, VEGF, AIF-1, JNK1, CB1, R1P140, TIF2, ANGPT1, ANGPT2, EIF4EBP2, CDK5, SLC13A5, Perilipin 1, Perilipin 2, Perilipin 3, Perilipin 4, HGF, GDF3, TNKs, KATNA1, ChREBP, ATF4, BASP-1, NNMT.

Embodiment 65

The duplex of any of embodiments 1-64, wherein the first modified oligonucleotide has a nucleobase sequence that is at least 80% complementary to the nucleobase sequence of the extra-hepatic nucleic acid target, when measured across the entire nucleobase sequence of the modified oligonucleotide.

Embodiment 66

The duplex of embodiment 65, wherein the first modified oligonucleotide has a nucleobase sequence that is at least 90% complementary to the nucleobase sequence of the extra-hepatic nucleic acid target, when measured across the entire nucleobase sequence of the modified oligonucleotide.

Embodiment 67

The duplex of embodiment 65, wherein the first modified oligonucleotide has a nucleobase sequence that is 100% complementary to the nucleobase sequence of the extra-hepatic nucleic acid target, when measured across the entire nucleobase sequence of the modified oligonucleotide.

Embodiment 68

The duplex of any of embodiments 1-55, wherein the first modified oligonucleotide has at least 8 contiguous nucleobases of any of the nucleobase sequences of SEQ ID NOs: 1, 2, 3, 4, 5, 6, 7, 8, 9, 10, 11, 12, 13, 14, 15, 16, 17, 18, 19, 20, 21, 22, or 23.

Embodiment 69

The duplex of any of embodiments 1-55, wherein the first modified oligonucleotide has at least 9 contiguous nucleobases of any of the nucleobase sequences of SEQ ID NOs: 1, 2, 3, 4, 5, 6, 7, 8, 9, 10, 11, 12, 13, 14, 15, 16, 17, 18, 19, 20, 21, 22, or 23.

Embodiment 70

The duplex of any of embodiments 1-55, wherein the first modified oligonucleotide has at least 10 contiguous nucleobases of any of the nucleobase sequences of SEQ ID NOs: 1, 2, 3, 4, 5, 6, 7, 8, 9, 10, 11, 12, 13, 14, 15, 16, 17, 18, 19, 20, 21, 22, or 23.

Embodiment 71

The duplex of any of embodiments 1-55, wherein the first modified oligonucleotide consists of the nucleobase sequence of any of SEQ ID NOs: 1, 2, 3, 4, 5, 6, 7, 8, 9, 10, 11, 12, 13, 14, 15, 16, 17, 18, 19, 20, 21, 22, or 23.

Embodiment 72

The duplex of any of embodiments 1-55, wherein the first modified oligonucleotide has at least 12 contiguous nucleobases of any of the nucleobase sequences of SEQ ID NOs: 1, 2, 3, 4, 5, 6, 7, 8, 9, 10, 11, 12, 13, 14, 15, 16, 17, 18, 19, 20, 21, 22, or 23.

Embodiment 73

The duplex of any of embodiments 1-72, wherein the first modified oligonucleotide does not have any 2'-deoxynucleosides.

Embodiment 74

The duplex of any of embodiments 1-72, wherein the first modified oligonucleotide comprises at least one modified nucleoside.

Embodiment 75

The duplex of embodiment 74, wherein the first modified oligonucleotide comprises a least one modified nucleoside comprising a modified sugar moiety.

Embodiment 76

The duplex of embodiment 75, wherein the first modified oligonucleotide comprises at least one modified nucleoside comprising a bicyclic sugar moiety.

Embodiment 77

The duplex of embodiment 76, wherein the first modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 78

The duplex of any of embodiments 73-77, wherein the first modified oligonucleotide comprises at least one modified nucleoside comprising a modified non-bicyclic sugar moiety.

Embodiment 79

The duplex of embodiment 78, wherein the first modified oligonucleotide comprises at least one modified nucleoside comprising a non-bicyclic sugar moiety comprising a 2'-MOE or 2'-O-Methyl modified sugar moiety.

Embodiment 80

The duplex of any of embodiments 73-79, wherein the first modified oligonucleotide comprises at least one modified nucleoside comprising a sugar surrogate.

Embodiment 81

The duplex of embodiment 80, wherein the first modified oligonucleotide comprises at least one modified nucleoside comprising a sugar surrogate selected from a morpholino, a PNA, a F-HNA, a THP, or a modified THP.

Embodiment 82

The duplex of any of embodiments 1-72 or 74-81, wherein the first modified oligonucleotide comprises a sugar motif having:
 a 5'-region consisting of 1-5 linked 5'-nucleosides;
 a central region consisting of 6-10 linked central region nucleosides; and
 a 3'-region consisting of 1-5 linked 3'-region nucleosides; wherein the nucleosides of the 5'-region, the 3'-region, and the central region are contiguous, and the central region nucleosides each comprise an unmodified DNA sugar moiety.

Embodiment 83

The duplex of embodiment 82, wherein each of the 5'-region nucleosides and each of the 3'-region nucleosides comprise a modified sugar moiety.

Embodiment 84

The duplex of any of embodiments 1-83, wherein the first modified oligonucleotide comprises at least one modified internucleoside linkage.

Embodiment 85

The duplex of embodiment 84, wherein each internucleoside linkage of the first modified oligonucleotide is a modified internucleoside linkage.

Embodiment 86

The duplex of embodiment 84 or 85 wherein at least one internucleoside linkage is a phosphorothioate internucleoside linkage.

Embodiment 87

The duplex of embodiment 84 or 86 wherein the first modified oligonucleotide comprises at least one unmodified phosphodiester internucleoside linkage.

Embodiment 88

The duplex of embodiment 87, wherein each internucleoside linkage is either an unmodified phosphodiester internucleoside linkage or a phosphorothioate internucleoside linkage.

Embodiment 89

The duplex of embodiment 85, wherein each internucleoside linkage is a phosphorothioate internucleoside linkage.

Embodiment 90

The duplex of any of embodiments 1-89, wherein the first modified oligonucleotide comprises at least one modified nucleobase.

Embodiment 91

The duplex of embodiment 90, wherein the first modified nucleobase is a 5-Methyl cytosine.

Embodiment 92

The duplex of any of embodiments 1-91 wherein each nucleobase of each nucleoside of the first modified oligonucleotide is either an unmodified nucleobase or is 5-Methyl cytosine.

Embodiment 93

The duplex of any of embodiments 1-92, wherein the first modified oligonucleotide consists of 12-22 linked nucleosides.

Embodiment 94

The duplex of any of embodiments 1-92, wherein the first modified oligonucleotide consists of 12-20 linked nucleosides.

Embodiment 95

The duplex of any of embodiments 1-92, wherein the first modified oligonucleotide consists of 14-20 linked nucleosides.

Embodiment 96

The duplex of any of embodiments 1-92, wherein the first modified oligonucleotide consists of 16-20 linked nucleosides.

Embodiment 97

The duplex of any of embodiments 1-92, wherein the first modified oligonucleotide consists of 18-20 linked nucleosides.

Embodiment 98

The duplex of any of embodiments 1-92, wherein the first modified oligonucleotide consists of 20 linked nucleosides.

Embodiment 99

The duplex of any of embodiments 1-92, wherein the first modified oligonucleotide consists of 19 linked nucleosides.

Embodiment 100

The duplex of any of embodiments 1-92, wherein the first modified oligonucleotide consists of 18 linked nucleosides.

Embodiment 101

The duplex of any of embodiments 1-92, wherein the first modified oligonucleotide consists of 17 linked nucleosides.

Embodiment 102

The duplex of any of embodiments 1-92, wherein the first modified oligonucleotide consists of 16 linked nucleosides.

Embodiment 103

The duplex of any of embodiments 1-102, wherein the second modified oligonucleotide does not have any 2' deoxynucleosides.

Embodiment 104

The duplex of any of embodiments 1-103, wherein the second modified oligonucleotide comprises at least one modified nucleoside.

Embodiment 105

The duplex of embodiment 104, wherein the second modified oligonucleotide comprises a least one modified nucleoside comprising a modified sugar moiety.

Embodiment 106

The duplex of embodiment 105, wherein the second modified oligonucleotide comprises at least one modified nucleoside comprising a bicyclic sugar moiety.

Embodiment 107

The duplex of embodiment 106, wherein the second modified oligonucleotide comprises at least one modified nucleoside comprising a bicyclic sugar moiety having a 2'-4' bridge, wherein the 2'-4' bridge is selected from —O—$CH_2$—; and —O—$CH(CH_3)$—.

Embodiment 108

The duplex of any of embodiments 103-107, wherein the second modified oligonucleotide comprises at least one modified nucleoside comprising a modified non-bicyclic sugar moiety.

Embodiment 109

The duplex of embodiment 108, wherein the first modified oligonucleotide comprises at least one modified nucleoside comprising a non-bicyclic sugar moiety comprising a 2'-MOE or 2'-O-Methyl modification.

Embodiment 110

The duplex of any of embodiments 103-109 wherein the second modified oligonucleotide does not comprise any nucleosides comprising 2'-OMe.

Embodiment 111

The duplex of any of embodiments 103-110, wherein the second modified oligonucleotide comprises at least one modified nucleoside comprising a sugar surrogate.

Embodiment 112

The duplex of embodiment 111, wherein the second modified oligonucleotide comprises at least one modified nucleoside comprising a sugar surrogate selected from a morpholino, a PNA, a F-HNA, a THP, or a modified THP.

Embodiment 113

The duplex of any of embodiments 104-112, wherein the second modified oligonucleotide has a sugar motif comprising:
a 5'-region consisting of 1-5 linked 5'-nucleosides;
a central region consisting of 6-10 linked central region nucleosides; and
a 3'-region consisting of 1-5 linked 3'-region nucleosides;
wherein the nucleosides of the 5'-region, the 3'-region, and the central region are contiguous; and the central region nucleosides each comprise an unmodified 2'-deoxy sugar moiety.

Embodiment 114

The duplex of embodiment 113 wherein each of the 5'-region nucleosides and each of the 3'-region nucleosides comprise a modified sugar moiety.

Embodiment 115

The duplex of embodiment 114, wherein the 5'-region nucleosides and the 3'-region nucleosides of the second modified oligonucleotide are selected from: F-RNA modified nucleosides, 2'-MOE modified nucleosides, LNA nucleosides, and cEt nucleosides.

Embodiment 116

The duplex of any of embodiments 104-112 wherein the second modified oligonucleotide has sugar motif comprising alternating 2'-deoxynucleosides and 2'-MOE modified nucleosides.

Embodiment 117

The duplex of any of embodiments 103-116, wherein the second modified oligonucleotide comprises at least one modified internucleoside linkage.

Embodiment 118

The duplex of embodiment 117, wherein each internucleoside linkage of the second modified oligonucleotide is a modified internucleoside linkage.

Embodiment 119

The duplex of embodiment 117 or 118 wherein at least one internucleoside linkage of the second oligonucleotide is a phosphorothioate internucleoside linkage.

Embodiment 120

The duplex of embodiment 117 or 119 wherein the second modified oligonucleotide comprises at least one unmodified phosphodiester internucleoside linkage.

Embodiment 121

The duplex of embodiment 120, wherein each internucleoside linkage of the second oligonucleotide is either an unmodified phosphodiester internucleoside linkage or a phosphorothioate internucleoside linkage.

Embodiment 122

The duplex of embodiment 118, wherein each internucleoside linkage of the second oligonucleotide is a phosphorothioate internucleoside linkage.

Embodiment 123

The duplex of any of embodiments 117 or 119-121 wherein the second oligonucleotide has a center region comprising unmodified phosphodiester internucleoside linkages.

Embodiment 124

The duplex of embodiment 123, wherein the second oligonucleotide has 1 or 2 terminal phosphorothioate linkages on one end or on both ends.

Embodiment 125

The duplex of any of embodiments 103-124, wherein the second modified oligonucleotide comprises at least one modified nucleobase.

Embodiment 126

The duplex of embodiment 125, wherein the second modified nucleobase is a 5-Methyl cytosine.

Embodiment 127

The duplex of any of embodiments 103-126 wherein each nucleobase of each nucleoside of the second modified oligonucleotide is either an unmodified nucleobase or is 5-Methyl cytosine.

Embodiment 128

The duplex of any of embodiments 103-127, wherein the second modified oligonucleotide consists of 12-22 linked nucleosides.

Embodiment 129

The duplex of any of embodiments 103-127, wherein the second modified oligonucleotide consists of 12-20 linked nucleosides.

Embodiment 130

The duplex of any of embodiments 103-127, wherein the second modified oligonucleotide consists of 14-20 linked nucleosides.

Embodiment 131

The duplex of any of embodiments 103-127, wherein the second modified oligonucleotide consists of 16-20 linked nucleosides.

Embodiment 132

The duplex of any of embodiments 103-127, wherein the second modified oligonucleotide consists of 18-20 linked nucleosides.

Embodiment 133

The duplex of any of embodiments 103-127, wherein the second modified oligonucleotide consists of 20 linked nucleosides.

Embodiment 134

The duplex of any of embodiments 103-127, wherein the second modified oligonucleotide consists of 19 linked nucleosides.

Embodiment 135

The duplex of any of embodiments 103-127, wherein the second modified oligonucleotide consists of 18 linked nucleosides.

Embodiment 136

The duplex of any of embodiments 103-127, wherein the second modified oligonucleotide consists of 17 linked nucleosides.

Embodiment 137

The duplex of any of embodiments 103-127, wherein the second modified oligonucleotide consists of 16 linked nucleosides.

Embodiment 138

The duplex of any of embodiments 1-137, wherein the conjugate linker comprises 1-5 linker-nucleosides.

Embodiment 139

The duplex of embodiment 138, wherein the conjugate linker comprises 3 linker-nucleosides.

Embodiment 140

The duplex of embodiment 139, wherein the 3 linker-nucleosides have a TCA motif.

Embodiment 141

The duplex of embodiment 138, wherein 1-5 linker-nucleosides do not comprise a TCA motif.

Embodiment 142

The duplex of any of embodiments 1-137, wherein the conjugate group does not comprise linker-nucleosides.

Embodiment 143

The duplex of any of embodiments 1-142, wherein the conjugate linker comprises a hexylamino group.

Embodiment 144

The duplex of any of embodiments 1-143, wherein the conjugate linker comprises a polyethylene glycol group.

Embodiment 145

The duplex of any of embodiments 1-144, wherein the conjugate linker comprises a triethylene glycol group.

Embodiment 146

The duplex of any of embodiments 1-145, wherein the conjugate linker comprises a phosphate group.

Embodiment 147

The duplex of any of embodiments 1-146, wherein the conjugate linker comprises:

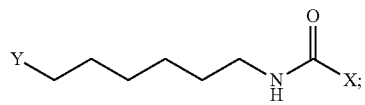

X directly or indirectly attaches to the conjugate moiety; and
Y directly or indirectly attaches to the second modified oligonucleotide.

Embodiment 148

The duplex of embodiment 147, wherein X comprises 0.

Embodiment 149

The duplex of embodiment 147 or 148, wherein Y comprises a phosphate group.

Embodiment 150

The duplex of any of embodiments 1-146, wherein the conjugate linker comprises:

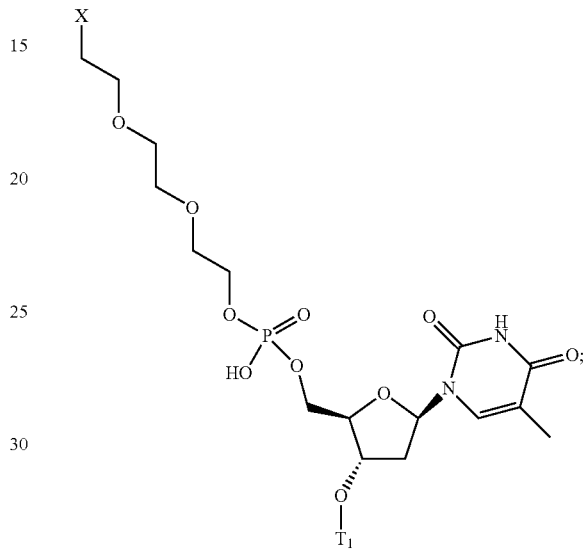

X directly or indirectly attaches to the conjugate moiety; and
$T_1$ comprises a linking group, nucleoside, or a modified oligonucleotide.

Embodiment 151

The duplex of any of embodiments 1-146, wherein the conjugate linker comprises:

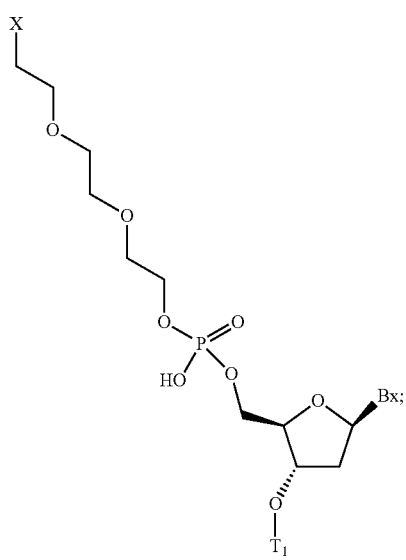

X directly or indirectly attaches to the conjugate moiety; and wherein $T_1$ comprises a nucleotide or a modified oligonucleotide; and $B_x$ is a modified or unmodified nucleobase.

Embodiment 152

The duplex of any of embodiments 1-151, wherein the conjugate moiety comprises lipophilic group.

Embodiment 153

The duplex of embodiment 152, wherein the lipophilic group is selected from among: cholesterol, $C_{10}$-$C_{26}$ saturated fatty acid, $C_{10}$-$C_{26}$ unsaturated fatty acid, $C_{10}$-$C_{26}$ alkyl, triglyceride, tocopherol, or cholic acid.

Embodiment 154

The duplex of embodiment 153, wherein the conjugate moiety is a saturated fatty acid or an unsaturated fatty acid.

Embodiment 155

The duplex of embodiment 153, wherein the conjugate moiety is C16 lipid.

Embodiment 156

The duplex of embodiment 153, wherein the conjugate moiety is C18 lipid.

Embodiment 157

The duplex of embodiment 153, wherein the conjugate moiety is C16 alkyl.

Embodiment 158

The duplex of embodiment 153, wherein the conjugate moiety is C18 alkyl.

Embodiment 159

The duplex of embodiment 153, wherein the conjugate moiety is cholesterol.

Embodiment 160

The duplex of embodiment 153, wherein the conjugate moiety is tocopherol.

Embodiment 161

The duplex of any of embodiments 1-160, wherein the conjugate group is attached to the second modified oligonucleotide at the 5'-end of the second modified oligonucleotide.

Embodiment 162

The duplex of any of embodiments 1-160, wherein the conjugate group is attached to the second modified oligonucleotide at the 3'-end of the second modified oligonucleotide.

Embodiment 163

The duplex of any of embodiments 1-162 comprising a terminal group.

Embodiment 164

An antisense compound consisting of the duplex of any of embodiments 1-163.

Embodiment 165

An antisense compound comprising the duplex of any of embodiments 1-163.

Embodiment 166

The antisense compound of embodiment 164 or 165 that is an RNase H antisense compound.

Embodiment 167

The antisense compound of embodiment 164 or 165 that is an RNAi antisense compound.

Embodiment 168

The antisense compound of any of embodiments 164-167 that is capable of reducing the amount or activity of the extra-hepatic nucleic acid target by at least 20% when tested at a concentration of 1.0 nM in a standard cell assay.

Embodiment 169

The antisense compound of embodiment 168 that is capable of reducing the amount or activity of the extra-hepatic nucleic acid target by at least 40% in the standard cell assay.

Embodiment 170

The antisense compound of embodiment 168 that is capable of reducing the amount or activity of the extra-hepatic nucleic acid target by at least 80% in the standard cell assay.

Embodiment 171

The antisense compound of any of embodiments 164-170 that is capable of reducing the amount or activity of the extra-hepatic nucleic acid target in an extra-hepatic tissue by at least 20% when provided at a dose of 100 mg/kg in a standard animal experiment.

Embodiment 172

The antisense compound of embodiment 171 that is capable of reducing the amount or activity of the extra-hepatic nucleic acid target in the extra-hepatic tissue by at least 40%.

Embodiment 173

The antisense compound of embodiment 171 that is capable of reducing the amount or activity of the extra-hepatic nucleic acid target in the extra-hepatic tissue by at least 80%.

Embodiment 174

The antisense compound of embodiment 164 or 165 that alters the RNA processing of the extra-hepatic nucleic acid target.

Embodiment 175

A method comprising contacting a cell with the duplex of any of embodiments 1-163.

Embodiment 176

A method comprising contacting a cell with the antisense compound of any of embodiments 164-174.

Embodiment 177

A method of modulating the amount or activity of an extra-hepatic nucleic acid target in a cell comprising contacting the cell with the duplex or antisense compound of any of embodiments 1-174 and thereby modulating the amount or activity of the extra-hepatic nucleic acid target in the cell.

Embodiment 178

The method of embodiment 177, wherein the amount or activity of the extra-hepatic nucleic acid target is reduced.

Embodiment 179

The method of any of embodiments 175-178, wherein the cell is in vitro.

Embodiment 180

The method of any of embodiments 175-178, wherein the cell is in an animal.

Embodiment 181

The method of embodiment 180, wherein the animal is a human.

Embodiment 182

A method of modulating the amount or activity of a hepatic nucleic acid target in a cell comprising contacting the cell with the duplex or antisense compound of any of embodiments 1-174 and thereby modulating the amount or activity of the hepatic nucleic acid target in the cell.

Embodiment 183

The method of embodiment 182, wherein the amount or activity of the extra-hepatic nucleic acid target is reduced.

Embodiment 184

The method of embodiment 182 or 183, wherein the cell is in vitro.

Embodiment 185

The method of embodiment 182 or 183, wherein the cell is in an animal.

Embodiment 186

The method of embodiment 185, wherein the animal is a human.

Embodiment 187

A pharmaceutical composition comprising a duplex of any embodiments 1-163 and a pharmaceutically acceptable carrier or diluent.

Embodiment 188

A pharmaceutical composition comprising an antisense compound of any of embodiments 164-174 and a pharmaceutically acceptable carrier or diluent.

Embodiment 189

A method comprising administering to an animal a pharmaceutical composition of embodiment 187 or 188.

Embodiment 190

A method of treating a disease associated with an extra-hepatic nucleic acid target comprising administering to an individual having or at risk for developing a disease associated with the extra-hepatic nucleic acid target a therapeutically effective amount of a pharmaceutical composition according to embodiment 187 or 188; and thereby treating the disease associated with the extra-hepatic nucleic acid target.

Embodiment 191

The method of embodiment 190, wherein the extra-hepatic nucleic acid target is selected from among: ATGL, CD40, CD36, DMPK, DNM2, DMD, DUX4, LMNA, ZFN9, SGLT2, or GCCR.

Embodiment 192

The method of embodiment 190, wherein the extra-hepatic nucleic acid target transcript is selected from among: Androgen Receptor (AR), ANGPTL3, DGAT2, eIF4E, Factor XI, FGFR4, GCCR, GCGR, GHR, PTP1B, SMRT, STAT3, Them1, TRPV4, FTO, MC4R, TMEM18, KCTD15, GNPDA2, SH2B1, MTCH2, NEGR1, BDNF, ETV5, Leptin, leptin receptor, FAIM2, KCNMA1, MAF, NRXN3, TFAP2B, MSRA, AGPAT2, BSCL2, AKT2, PPARγ, LMNA, ZMPSTE24, DGAT1, TNFα, IL-6, Resistin, PAI-1, TBC1D1, METAP2, VEGF, AIF-1, JNK1, CB1, RIP140, TIF2, ANGPT1, ANGPT2, EIF4EBP2, CDK5, SLC13A5, Perilipin 1, Perilipin 2, Perilipin 3, Perilipin 4, HGF, GDF3, TNKs, KATNA1, ChREBP, ATF4, BASP-1, NNMT.

Embodiment 193

The method of embodiment 190, wherein the extra-hepatic nucleic acid target transcript is not selected from among: Androgen Receptor (AR), ANGPTL3, DGAT2, eIF4E, Factor XI, FGFR4, GCCR, GCGR, GHR, PTP1B, SMRT, STAT3, Them1, TRPV4, FTO, MC4R, TMEM18, KCTD15, GNPDA2, SH2B1, MTCH2, NEGR1, BDNF, ETV5, Leptin, leptin receptor, FAIM2, KCNMA1, MAF, NRXN3, TFAP2B, MSRA, AGPAT2, BSCL2, AKT2, PPARγ, LMNA, ZMPSTE24, DGAT1, TNFα, IL-6, Resistin, PAI-1, TBC1D1, METAP2, VEGF, AIF-1, JNK1, CB1, RIP140, TIF2, ANGPT1, ANGPT2, EIF4EBP2, CDK5, SLC13A5, Perilipin 1, Perilipin 2, Perilipin 3, Perilipin 4, HGF, GDF3, TNKs, KATNA1, ChREBP, ATF4, BASP-1, NNMT.

Embodiment 194

The method of any of embodiments 190-193, wherein at least one symptom of a disease associated with an extra-hepatic nucleic acid target is ameliorated.

Embodiment 195

The method of any of embodiments 190-194, wherein the disease is selected from among: diabetes, metabolic syndrome, cardiac disease, muscular dystrophy, myotonic dystrophy, Becker muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, or oculopharyngeal muscular dystrophy.

Embodiment 196

The method of any of embodiments 189-195 wherein the amount or activity of the extra-hepatic nucleic acid target is modulated in at least one tissue type other than liver.

Embodiment 197

The method of embodiment 196, wherein the amount of activity of the extra-hepatic nucleic acid target is modulated in at least two tissue types.

Embodiment 198

The method of embodiment 197, wherein at least one of the at least two tissue types is selected from among: liver, skeletal muscle, cardiac muscle, smooth muscle, adipose, white adipose, spleen, bone, intestine, adrenal, testes, ovary, pancreas, pituitary, prostate, skin, uterus, bladder, brain, glomerulus, distal tubular epithelium, breast, lung, heart, kidney, ganglion, frontal cortex, spinal cord, trigeminal ganglia, sciatic nerve, dorsal root ganglion, epididymal fat, diaphragm, and colon.

Embodiment 199

The method of embodiment 198, wherein at least two tissue types are selected from among: liver, skeletal muscle, cardiac muscle, smooth muscle, adipose, white adipose, spleen, bone, intestine, adrenal, testes, ovary, pancreas, pituitary, prostate, skin, uterus, bladder, brain, glomerulus, distal tubular epithelium, breast, lung, heart, kidney, ganglion, frontal cortex, spinal cord, trigeminal ganglia, sciatic nerve, dorsal root ganglion, epididymal fat, diaphragm, and colon.

Embodiment 200

A method of treating a multi-tissue disease or condition, comprising administering a therapeutically effective amount of the pharmaceutical composition of embodiment 187 or 188 to a subject, and thereby modulating the amount or activity of a target nucleic acid in two or more tissues.

Embodiment 201

A method of treating a disease or condition, comprising administering a therapeutically effective amount of the pharmaceutical composition of embodiment 187 or 188 to a subject, and thereby modulating the amount or activity of a target nucleic acid in two or more cell types.

Embodiment 202

A method of treating a multi-tissue disease or condition, comprising administering a therapeutically effective amount of the pharmaceutical composition of embodiment 187 or 188 to a subject, and thereby modulating the amount or activity of a target nucleic acid in two or more cell types.

Embodiment 203

The method of embodiment 201 or 202, wherein the two or more cell types are selected from among: hepatocytes, white fat cells, brown fat cells, adipocytes, macrophages, cancer cells, tumor cells, smooth muscle cells, lymphocytes, and heart muscle cells.

Embodiment 204

The method of any of embodiments 189-203, wherein the pharmaceutical composition is administered subcutaneously.

Embodiment 205

The method of any of embodiments 189-203, wherein the pharmaceutical composition is administered intravenously.

Embodiment 206

The method of any of embodiments 189-203, wherein the pharmaceutical composition is administered by parenteral administration.

Embodiment 207

The method of any of embodiments 189-203, wherein the pharmaceutical composition is administered by intraperitoneal administration.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"Antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound. In certain embodiments, antisense activity is a change in splicing of a pre-mRNA nucleic acid target. In certain embodiments, antisense activity is an increase in the amount or expression of a target nucleic acid or protein encoded by such target nucleic acid compared to target nucleic acid levels or target protein levels in the absence of the antisense compound.

"Antisense compound" means a compound comprising an antisense oligonucleotide and optionally one or more additional features, such as a conjugate group or terminal group.

"Antisense oligonucleotide" means an oligonucleotide that (1) has a nucleobase sequence that is at least partially complementary to a target nucleic acid and that (2) is capable of producing an antisense activity in a cell or animal.

"Ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

"Bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"Cleavable moiety" means a bond or group of atoms that is cleaved under physiological conditions, for example, inside a cell, an animal, or a human.

"Complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include, but unless otherwise specific are not limited to, adenine (A) and thymine (T), adenine (A) and uracil (U), cytosine (C) and guanine (G), 5-methyl cytosine (IT) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

"Conjugate group" means a group of atoms that is directly or indirectly attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Duplex" means two oligomeric compounds that are paired. In certain embodiments, the two oligomeric compounds are paired via hybridization of complementary nucleobases.

"Extra-hepatic cell type" means a cell type that is not a hepatocyte.

"Extra-hepatic nucleic acid target" means a target nucleic acid that is expressed in tissues other than liver. In certain embodiments, extra-hepatic nucleic acid targets are not expressed in the liver or not expressed in the liver at a significant level. In certain embodiments, extra-hepatic nucleic acid targets are expressed outside the liver and also in the liver.

"Extra-hepatic tissue" means a tissue other than liver.

"Fully modified" in reference to a modified oligonucleotide means a modified oligonucleotide in which each sugar moiety is modified. "Uniformly modified" in reference to a modified oligonucleotide means a fully modified oligonucleotide in which each sugar moiety is the same. For example, the nucleosides of a uniformly modified oligonucleotide can each have a 2'-MOE modification but different nucleobase modifications, and the internucleoside linkages may be different.

"Gapmer" means an antisense oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage.

"Linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

"Lipophilic group" or "lipophilic" in reference to a chemical group means a group of atoms that is more soluble in lipids or organic solvents than in water and/or has a higher affinity for lipids than for water. In certain embodiments, lipophilic groups comprise a lipid. As used herein "lipid" means a molecule that is not soluble in water or is less soluble in water than in organic solvents. In certain embodiments, compounds of the present invention comprise lipids selected from saturated or unsaturated fatty acids, steroids, fat soluble vitamins, phospholipids, sphingolipids, hydrocarbons, mono-, di-, and tri-glycerides, and synthetic derivatives thereof.

"Non-bicyclic modified sugar" or "non-bicyclic modified sugar moiety" means a modified sugar moiety that comprises a modification, such as a substitutent, that does not form a bridge between two atoms of the sugar to form a second ring.

"Linked nucleosides" are nucleosides that are connected in a continuous sequence (i.e. no additional nucleosides are present between those that are linked).

"Mismatch" or "non-complementary" means a nucleobase of a first oligonucleotide that is not complementary with the corresponding nucleobase of a second oligonucleotide or target nucleic acid when the first and second oligomeric compound are aligned.

"MOE" means methoxyethyl. "2'-MOE" means a —OCH$_2$CH$_2$OCH$_3$ group at the 2' position of a furanosyl ring.

"Motif" means the pattern of unmodified and/or modified sugar moieties, nucleobases, and/or internucleoside linkages, in an oligonucleotide.

"Multi-tissue disease or condition" means a disease or condition affects or is effected by more than one tissue. In treating a multi-tissue disease or condition, it is desirable to affect more than one tissue type. In certain embodiments, treatment of disease or condition may be enhanced by treating the disase or condition in multiple tissues. For example, in certain embodiments, a disease or condition may manifest itself in the liver tissue and the muscle tissue. In certain embodiments, treating the disease or condition in the liver tissue and the muscle tissue will be more effective than treating the disease in either the liver tissue or the muscle tissue.

"Naturally occurring" means found in nature.

"Nucleobase" means an unmodifiednucleobase or a modified nucleobase. As used herein a an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

"Nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include a basic nucleosides, which lack a nucleobase.

"Oligomeric compound" means a compound consisting of an oligonucleotide and optionally one or more additional features, such as a conjugate group or terminal group.

"Oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

"Pharmaceutically acceptable carrier or diluent" means any substance suitable for use in administering to an animal Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

"Pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

"Pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

"Phosphorus moiety" means a group of atoms comprising a phosphorus atom. In certain embodiments, a phosphorus moiety comprises a mono-, di-, or tri-phosphate, or phosphorothioate.

"Prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

"RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

"Single-stranded" in reference to an oligomeric compound means such a compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case it would no longer be single-stranded.

"Standard cell assay" means the assay described in Example 1 and reasonable variations thereof "Standard in vivo experiment" means the procedure described in Example 5 and reasonable variations thereof.

"Sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Target nucleic acid" means a naturally occurring, identified nucleic acid. In certain embodiments, target nucleic acids are endogenous cellular nucleic acids, including, but not limited to RNA transcripts, pre-mRNA, mRNA, microRNA. In certain embodiments, target nucleic acids are viral nucleic acids. In certain embodiments, target nucleic acids are nucleic acids that an antisense compound is designed to affect.

"Target region" means a portion of a target nucleic acid to which an antisense compound is designed to hybridize.

"TCA motif" means three nucleosides having the nucleobase sequence TCA (5'-3'). Such nucleosides may have modified sugar moieties and/or modified internucleosides linkages. Unless otherwise indicated, the nucleosides of TCA motifs comprise unmodified 2'-deoxy sugar moieties and unmodified phosphodiester internucleoside linkages.

"Terminal group" means a chemical group or group of atoms that is covalently linked to a terminus of an oligonucleotide.

"CNS" means central nervous system. The CNS includes, the spine and the brain and the cerebrospinal fluid.

"Cerebrospinal fluid" or "CSF" means the fluid filling the space around the brain and spinal cord.

"Nervous system" means the network of nerve cells and fibers that transmits nerve impulses between parts of the body. The nervous system includes glial cells and neurons. The nervous system includes the central nervous system and the peripheral nervous system.

I. Certain Oligonucleotides

In certain embodiments, the invention provides a duplex comprising a first oligomeric compound and a second oligomeric compound. In certain embodiments an oligomeric compound comprises an oligonucleotide, which consists of linked nucleosides. Oligonucleotides may be unmodified oligonucleotides (RNA or DNA) or may be modified oligonucleotides. Modified oligonucleotides, for example the first modified oligonucleotide or the second modified oligonucleotide, comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modifed sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)-N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)-N(H)CH_3$ ("NMA").

In certain embodiments, a 2'-substituted nucleoside or 2'-non-bicyclic modified nucleoside comprises a sugar moiety comprising a non-bridging 2'-substituent group selected from: F, $OCH_3$, and $OCH_2CH_2OCH_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-($CH_2$)$_2$-2', 4'-($CH_2$)$_3$-2', 4'-$CH_2$—O-2' ("LNA"), 4'-$CH_2$—S-2', 4'-($CH_2$)$_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., J. Org. Chem., 2009, 74, 118-134), 4'-$CH_2$—C($=CH_2$)-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: $-[C(R_a)(R_b)]_n-$, $-[C(R_a)(R_b)]_n-O-$, $-C(R_a)=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C(=O)-H$), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C(=O)-H$), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

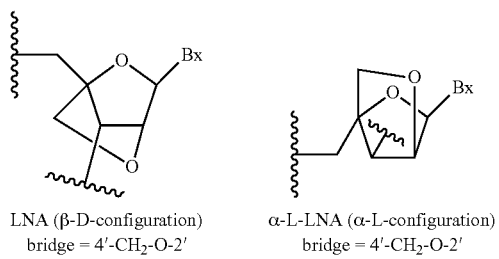

LNA (β-D-configuration)
bridge = 4'-CH₂-O-2'

α-L-LNA (α-L-configuration)
bridge = 4'-CH₂-O-2'

α-L-methyleneoxy (4'-CH₂—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

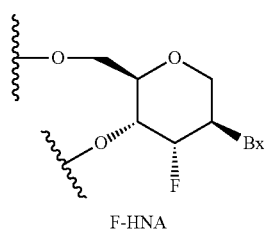

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

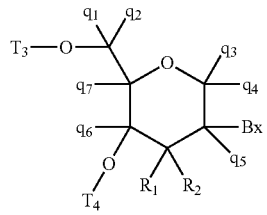

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

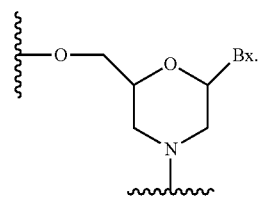

In certain embodiments, morpholinos may be modified, for example by adding or altering various substituent groups from the above morpholino structure. Such sugar surrogates are referred to herein as "modifed morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

1. Certain Modified Nucleobases

In certain embodiments, the first modified oligonucleotide comprises one or more nucleoside comprising an unmodified nucleobase. In certain embodiments, the second modified oligonucleotide comprises one or more nucleoside comprising an unmodified nucleobase. In certain embodiments, modified oligonucleotides, for example the first modified oligonucleotide or the second modified oligonucleotide, comprise one or more nucleoside comprising a modified nucleobase. In certain embodiments, modified oligonucleotides, for example the first modified oligonucleotide or the second modified oligonucleotide, comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. In certain embodiments, nucleosides of the first modified oligonucleotide may be linked together using any internucleoside linkage. In certain embodiments, nucleosides of the second modified oligonucleotide may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—CH$_2$—N(CH$_3$)—O—CH$_2$—), thiodiester, thionocarbamate (—O—C(═O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(═O)—N(H)-5'), amide-4 (3'-CH$_2$—N(H)—C(═O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., *ACS Symposium Series* 580; Chapters 3 and 4, 40-65). Further neutral internucleoside linkages include nonionic linkages comprising mixed N, O, S and CH$_2$ component parts.

C. Certain Motifs

In certain embodiments, the first modified oligonucleotide comprises one or more modified nucleoside comprising a modified sugar. In certain embodiments, the first modified oligonucleotide comprises one or more modified nucleosides comprising a modified nucleobase. In certain embodiments, the first modified oligonucleotide comprises one or more modified internucleoside linkage. In such embodiments, the modified, unmodified, and differently modified sugar moieties, nucleobases, and/or internucleoside linkages of the first modified oligonucleotide define a pattern or motif. In certain embodiments, the patterns of sugar moieties, nucleobases, and internucleoside linkages are each independent of one another. Thus, the first modified oligonucleotide may be described by its sugar motif, nucleobase motif and/or internucleoside linkage motif (as used herein, nucleobase motif describes the modifications to the nucleobases independent of the sequence of nucleobases).

In certain embodiments, the second modified oligonucleotide comprises one or more modified nucleoside comprising a modified sugar. In certain embodiments, the second modified oligonucleotide comprises one or more modified nucleosides comprising a modified nucleobase. In certain embodiments, the second modified oligonucleotide comprises one or more modified internucleoside linkage. In such embodiments, the modified, unmodified, and differently modified sugar moieties, nucleobases, and/or internucleoside linkages of the second modified oligonucleotide define a pattern or motif. In certain embodiments, the patterns of sugar moieties, nucleobases, and internucleoside linkages are each independent of one another. Thus, the second modified oligonucleotide may be described by its sugar motif, nucleobase motif and/or internucleoside linkage motif (as used herein, nucleobase motif describes the modifications to the nucleobases independent of the sequence of nucleobases).

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides, for example the first modified oligonucleotide, comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, the first modified oligonucleotide and/or the second modified oligonucleotide comprise or consist of a region having a fully modified sugar motif. In such embodiments, each nucleoside of the fully modified region of the modified oligonucleotide comprises a modified sugar moiety. In certain such embodiments, each nucleoside to the entire modified oligonucleotide (either the first modified oligonucleotide and/or the second modified oligonucleotide) comprises a modified sugar moiety. In certain embodiments, modified oligonucleotides (either the first modified oligonucleotide and/or the second modified oligonucleotide) comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides (including the first modified oligonucleotide and/or the second modified oligonucleotide) comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides (for example the first modified oligonucleotide or the second modified oligonucleotide) comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine. In certain embodiments, the first modified oligonucleotide has a gapmer motif. In certain embodiments, the first modified oligonucleotide has a gapmer motif and the second modified oligonucleotide does not have a gapmer motif. In certain embodiments, the first modified oligonucleotide has a gapmer motif and the second modified oligonucleotide has a fully modified motif.

3. Certain Internucleoside Linkage Motifs

In certain embodiments, oligonucleotides, for example the first modified oligonucleotide and/or the second modified oligonucleotide, comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, essentially each internucleoside linking group of the first modified oligonucleotide is a phosphate internucleoside linkage (P=O). In certain embodiments, each internucleoside linking group of the first modified oligonucleotide is a phosphorothioate (P=S). In certain embodiments, essentially each internucleoside linking group of the second modified oligonucleotide is a phosphate internucleoside linkage (P=O). In certain embodiments, each internucleoside linking group of the second modified oligonucleotide is a phosphorothioate (P=S). In certain embodiments, each internucleoside linking group of the first modified oligonucleotide is independently selected from a phosphorothioate and phosphate internucleoside linkage. In certain embodiments, each internucleoside linking group of the second modified oligonucleotide is independently selected from a phosphorothioate and phosphate internucleoside linkage. In certain embodiments, the sugar motif of the first modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

D. Certain Lengths

In certain embodiments, oligonucleotides (including modified oligonucleotides) can have any of a variety of ranges of lengths. In certain embodiments, the first modified oligonucleotide can have any of a variety of ranges of lengths. In certain embodiments, the second modified oligonucleotide can have any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides E. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified or a first modified oligonucleotide or a second modified oligonucleotide) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides, including a first modified oligonucleotide or a second modified oligonucleotide, are covalently attached to one or more conjugate groups. In certain embodiments, a second modified oligonucleotide is covalently attached to one or more conjugate groups. In certain embodiments, a second modified oligonucleotide is covalently attached to one or more conjugate groups and the first modified oligonucleotide is not attached to a conjugate group. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Certain Antisense Compounds

In certain embodiments, the present invention provides antisense compounds, which comprise or consist of an oligomeric compound comprising an antisense oliognucleotide, having a nucleobase sequences complementary to that of a target nucleic acid. In certain embodiments, antisense compounds are single-stranded. Such single-stranded antisense compounds typically comprise or consist of an oligomeric compound that comprises or consists of a modified oligonucleotide and optionally a conjugate group. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprises a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

IV. Certain Duplexes

In certain embodiments, the present invention provides duplexes comprising a first oligomeric compound comprising a first modified oligonucleotide and a second oligomeric compound comprising a second oligonucleotide, wherein the first and second modified oligonucleotides comprise regions of complementarity sufficient to form a duplex. In certain such embodiments, the first modified oligonucleotide is complementary to a target nucleic acid. In certain such embodiments, the first modified oligonucleotide is a gapmer as described above. Thus, in such embodiments, the first oligomeric compound is capable of hybridizing to a target nucleic acid and eliciting cleavage of the target nucleic acid by RNase H. In certain such embodiments, the second oligomeric compound improves a property of the first oligomeric compound compared to the property in the absence of the second oligomeric compound. In certain embodiments, that improved property is one or more of: distribution to a target tissue, uptake into a target cell, potency, and efficacy. In certain embodiments, the target tissue is liver (hepatic). In certain embodiments, the target tissue is other than liver (extra-hepatic). In certain embodiments, it is desirable to reduce target in more than one tissue. In certain such embodiments, it is desirable to reduce target in the liver and one or more other tissues. In certain embodiments, it is desirable to reduce target in more than one extra-hepatic tissue.

In certain embodiments, the first oligonucleotide of a duplex is a gapmer. In certain such embodiments, the wings of the gapmer comprise 2'-MOE modified nucleosides. In certain embodiments, the wings of the gapmer comprise cEt nucleosides. In certain embodiments the wings of the gapmer comprise LNA nucleosides. In certain embodiments, the wings of a gapmer comprise at least one 2'-MOE modified nucleoside and at least one bicyclic nucleoside. In certain such embodiments, each such bicyclic nucleoside is selected from among an LNA nucleosid and a cEt nucleoside. In certain embodiments, the gap constitutes 7-10 2'-deoxynucleosides.

In certain embodiments, the second oligonucleotide comprises at least one 2'-MOE nucleoside. In certain embodiments, the second oligonucleotide comprises 2'-MOE and 2'-deoxynucleosides. In certain embodiments, the second oligonucleotide has sugar motif of alternating modification types (including no modification). In certain such embodiments, the sugar motif of the second oligonucleotide alternates between 2'-MOE nucleosides and 2'-deoxynucleosides. In certain embodiments, the second oligonucleotide has a sugar motif similar to a gapmer (as described above) except that it may not elicit cleavage of a target nucleic acid. Such gapmer-like motifs have a central region and flanking wing regions. In certain such embodiment, the central region is comprises of 2'-deoxynucleosides and the wing regions are 2'-MOE modified nucleosides. The internucleoside linkages of the second oligonucleotide may be modified or phosphodiester. In certain embodiments, the internucleoside linkages of the second oligonucleotide follow a gapmer-like motif-phosphorothioate wings and phosphdiester in the center. Such internucleoside linkage motif may or may not track the sugar motif. Though duplexes comprising second oligomeric compounds with second oligonucleotides having central regions comprising RNA are shown herein to have enhanced activity (compared to the first oligomeric compound alone and not in a duplex) it is noted that such oligonucleotides comprising RNA are expensive to manufacture and relatively unstable when compared to oligonucleotides that comprise modified nucleosides or DNA nucleosides.

In certain embodiments, at least one of the first and second oligomeric compounds comprises a conjugate group (as described above). Typically, the second oligomeric compound comprises a conjugate group. The conjugate group may be attached at either end of the oligomeric compound. In certain embodiments, a conjugate group is attached to both ends.

V. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism (SNP). In certain such embodiments, the antisense compound is capable of modulating expression of one allele of the SNP-containing target nucleic acid to a greater or lesser extent than it modulates another allele. In certain embodiments, an antisense compound hybridizes to a (SNP)-containing target nucleic acid at the single-nucleotide polymorphism site.

In certain embodiments, antisense compounds are at least partially complementary to more than one target nucleic acid. For example, antisense compounds of the present invention may mimic microRNAs, which typically bind to multiple targets.

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, the oligomeric compounds of antisense compounds comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

B. Certain Target Nucleic Acids in Certain Tissues

In certain embodiments, antisense compounds comprise or consist of an oligonucleotide comprising a region that is complementary to a target nucleic acid, wherein the target nucleic acid is expressed in an extra-hepatic tissue. Extra-hepatic tissues include, but are not limited to: skeletal muscle, cardiac muscle, smooth muscle, adipose, white adipose, spleen, bone, intestine, adrenal, testes, ovary, pancreas, pituitary, prostate, skin, uterus, bladder, brain, glomerulus, distal tubular epithelium, breast, lung, heart, kidney, ganglion, frontal cortex, spinal cord, trigeminal ganglia, sciatic nerve, dorsal root ganglion, epididymal fat, diaphragm, pancreas, and colon.

A. Certain First Modified Oligonucleotides

In certain embodiments, disclosed here in are first modified oligonucleotides designed to target certain nucleic acid targets. Tables A and B below describe certain modified oligonucleotides targeted to certain nucleic acid transcripts. In Tables A and B below, subscript "s" represents a phosphorothioate internucleoside linkage, subscript "o" represents a phosphate internucleoside linkage, subscript "d" represents a 2'-deoxynucleoside, subscript "e" represents a 2'-MOE modified nucleoside, and subscript "k" represents a cEt modified nucleoside. In tables A and B below, superscript "m" before a C represents a 5-methylcysteine

TABLE A

Certain First Modified Oligonucleotides

| Target | Isis No. | Sequence (5'-3') | Motif | SEQ ID NO: |
|---|---|---|---|---|
| CRP | 329993 | AGCATAGTTAACGAGCTCCC | 5-10-5 MOE | 14 |
| PTPB1B | 404173 | AATGGTTTATTCCATGGCCA | 5-10-5 MOE | 15 |
| GCCR | 426115 | GCAGCCATGGTGATCAGGAG | 5-10-5 MOE | 16 |

TABLE A-continued

Certain First Modified Oligonucleotides

| Target | Isis No. | Sequence (5'-3') | Motif | SEQ ID NO: |
|---|---|---|---|---|
| GCGR | 449884 | GGTTCCCGAGGTGCCCA | 3-10-4 MOE | 17 |
| FGFR4 | 463588 | GCACACTCAGCAGGACCCCC | 5-10-5 MOE | 18 |
| GHr | 532401 | CCACCTTTGGGTGAATAGCA | 5-10-5 MOE | 19 |
| DGAT2 | 484137 | TGCCATTTAATGAGCTTCAC | 5-10-5 MOE | 20 |
| DMPK | 598769 | TCCCGAATGTCCGACA | Mixed wing | 21 |
| CFB | 696844 | ATCCCACGCCCCTGTCCAGC | 5-10-5 MOE GalNAc | 22 |

TABLE B

Certain First Modified Oligonucleotides

| Target | Isis No. | Motif (5'-3') |
|---|---|---|
| CRP | 329993 | $A_{es}G_{es}{}^mC_{es}A_{es}T_{es}A_{ds}G_{ds}T_{ds}T_{ds}A_{ds}A_{ds}{}^mC_{ds}G_{ds}A_{ds}G_{ds}{}^mC_{es}T_{es}{}^mC_{es}{}^mC_{es}{}^mC_{e}$ |
| PTPB1B | 404173 | $A_{es}A_{es}T_{es}G_{es}G_{es}T_{ds}T_{ds}T_{ds}A_{ds}T_{ds}T_{ds}{}^mC_{ds}{}^mC_{ds}A_{ds}T_{ds}G_{es}G_{es}{}^mC_{es}{}^mC_{es}A_{e}$ |
| GCCR | 426115 | $G_{es}{}^mC_{es}A_{es}G_{es}{}^mC_{es}{}^mC_{ds}A_{ds}T_{ds}G_{ds}G_{ds}T_{ds}G_{ds}A_{ds}T_{ds}{}^mC_{ds}A_{es}G_{es}G_{es}A_{es}G_{e}$ |
| GCGR | 449884 | $G_{es}G_{es}T_{es}T_{ds}{}^mC_{ds}{}^mC_{ds}{}^mC_{ds}G_{ds}A_{ds}G_{ds}G_{ds}T_{ds}G_{ds}{}^mC_{es}{}^mC_{es}{}^mC_{es}A_{e}$ |
| FGFR4 | 463588 | $G_{es}{}^mC_{es}A_{es}{}^mC_{es}A_{es}{}^mC_{ds}T_{ds}{}^mC_{ds}A_{ds}G_{ds}{}^mC_{ds}A_{ds}G_{ds}G_{ds}A_{ds}{}^mC_{es}{}^mC_{es}{}^mC_{es}{}^mC_{es}{}^mC_{e}$ |
| GHr | 532401 | $^mC_{es}{}^mC_{es}A_{es}{}^mC_{es}{}^mC_{es}T_{ds}T_{ds}T_{ds}G_{ds}G_{ds}G_{ds}T_{ds}G_{ds}A_{ds}A_{ds}T_{es}A_{es}G_{es}{}^mC_{es}A_{e}$ |
| DGAT2 | 484137 | $T_{es}G_{es}{}^mC_{es}{}^mC_{es}A_{es}T_{ds}T_{ds}T_{ds}A_{ds}A_{ds}T_{ds}G_{ds}A_{ds}G_{ds}{}^mC_{ds}T_{es}T_{es}{}^mC_{es}A_{es}{}^mC_{e}$ |
| DMPK | 598769 | $T_{es}{}^mC_{es}{}^mC_{ks}{}^mC_{ks}G_{ds}A_{ds}A_{ds}T_{ds}G_{ds}T_{ds}{}^mC_{ds}{}^mC_{ds}G_{ks}A_{ks}{}^mC_{es}A_{e}$ |
| CFB | 696844 | $A_{es}T_{es}{}^mC_{es}{}^mC_{es}{}^mC_{es}A_{ds}{}^mC_{ds}G_{ds}{}^mC_{ds}{}^mC_{ds}{}^mC_{ds}T_{ds}G_{ds}T_{ds}{}^mC_{es}{}^mC_{es}A_{es}G_{es}{}^mC_{e}$ |

The first modified oligonucleotides provided above can be paired with the second modified oligonucleotide of a second oligomeric compound to form a duplex.

I. Certain Pharmaceutical Compositions

In certain embodiments, the present invention provides pharmaceutical compositions comprising one or more antisense compound or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$c indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated. Unless otherwise indicated, compounds described herein are intended to include corresponding salt forms.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effects of Duplexes Comprising a Lipophilic Conjugate Group In Vivo

Duplexes, each consisting of two oligomeric compounds, are described in the table below. One oligomeric compound of each duplex comprises an antisense oligonucleotide (Isis No. 626112) that is complementary to both human and mouse Metastasis Associated Lung Adenocarcinoma Transcript 1 (MALAT-1) transcripts. The other oligomeric compound of each duplex comprises an oligonucleotide and a lipophilic conjugate group. The effects of the duplexes on MALAT-1 expression were tested in vivo. Wild type C57bl/6 mice each received an intravenous injection, via the tail vein, of a duplex listed in the table below, Isis No. 626112 alone as a control, or saline vehicle alone. Each injection contained 100 mg/kg of the antisense oligonucleotide (Isis No. 626112). Each treatment group consisted of four mice. Eight days after the injection, the animals were sacrificed. MALAT-1 RNA expression was analyzed in liver, kidney, lung, trigeminal ganglia, frontal cortex, and spinal cord by RT-qPCR and normalized to total RNA using RiboGreen (Thermo Fisher Scientific, Carlsbad, Calif.). The average results for each group are shown below as the percent normalized MALAT-1 RNA levels relative to average results for the vehicle treated animals.

TABLE 1

MALAT-1 expression in vivo

| Duplex | Isis No. | Sequence (5' to 3') | MALAT-1 RNA level (% Vehicle) | | | | | | SEQ ID NO. |
|---|---|---|---|---|---|---|---|---|---|
| | | | Liver | Kidney | Lung | Ganglia | Fr. Cor. | Sp. Cord | |
| n/a | 626112 | $G_{es}$ $^mC_{eo}$ $^mC_{eo}$ $A_{eo}$ $G_{eo}$ $G_{ds}$ $^mC_{ds}$ $T_{ds}$ $G_{ds}$ $G_{ds}$ $T_{ds}$ $T_{ds}$ $A_{ds}$ $T_{ds}$ $G_{ds}$ $A_{eo}$ $^mC_{eo}$ $T_{es}$ $^mC_{es}$ $A_e$ | 26 | 67 | 62 | 65 | 101 | 104 | 1 |
| 1 | 626112 | $G_{es}$ $T_{eo}$ $T_{eo}$ $A_{eo}$ $G_{eo}$ $G_{ds}$ $^mC_{ds}$ $T_{ds}$ $G_{ds}$ $G_{ds}$ $T_{ds}$ $T_{ds}$ $A_{ds}$ $T_{ds}$ $G_{ds}$ $A_{eo}$ $^mC_{eo}$ $T_{es}$ $^mC_{es}$ $A_e$ | 59 | 59 | 89 | 55 | 119 | 110 | 1 |
| | 719228 | Toco-TEG-$U_{ms}$ $G_{ms}$ $A_{ro}$ $G_{ro}$ $U_{ro}$ $C_{ro}$ $A_{ro}$ $U_{ro}$ $A_{ro}$ $A_{ro}$ $G_{ro}$ $C_{ro}$ $A_{ro}$ $G_{ro}$ $C_{ro}$ $C_{ro}$ $U_{ro}$ $G_{rs}$ $G_{ms}$ $C_m$ | | | | | | | 2 |
| 2 | 626112 | $G_{es}$ $T_{eo}$ $T_{eo}$ $A_{eo}$ $G_{eo}$ $G_{ds}$ $^mC_{ds}$ $T_{ds}$ $G_{ds}$ $G_{ds}$ $T_{ds}$ $T_{ds}$ $A_{ds}$ $T_{ds}$ $G_{ds}$ $A_{eo}$ $^mC_{eo}$ $T_{es}$ $^mC_{es}$ $A_e$ | 38 | 39 | 76 | 47 | 107 | 88 | 1 |
| | 719232 | C10-TEG-$U_{ms}$ $G_{ms}$ $A_{ro}$ $G_{ro}$ $C_{ro}$ $A_{ro}$ $G_{ro}$ $C_{ro}$ $C_{ro}$ $U_{ro}$ $G_{rs}$ $G_{ms}$ $C_m$ | | | | | | | 2 |
| 3 | 626112 | $G_{es}$ $^mC_{eo}$ $^mC_{eo}$ $A_{eo}$ $G_{eo}$ $G_{ds}$ $^mC_{ds}$ $T_{ds}$ $G_{ds}$ $G_{ds}$ $T_{ds}$ $T_{ds}$ $A_{ds}$ $T_{ds}$ $G_{ds}$ $A_{eo}$ $^mC_{eo}$ $T_{es}$ $^mC_{es}$ $A_e$ | 27 | 63 | 86 | 38 | 120 | 75 | 1 |
| | 719233 | C16-TEG-$U_{ms}$ $G_{ms}$ $A_{ro}$ $G_{ro}$ $U_{ro}$ $C_{ro}$ $A_{ro}$ $U_{ro}$ $A_{ro}$ $A_{ro}$ $C_{ro}$ $C_{ro}$ $A_{ro}$ $G_{ro}$ $C_{ro}$ $C_{ro}$ $U_{ro}$ $G_{rs}$ $G_{ms}$ $C_m$ | | | | | | | 2 |
| 4 | 626112 | $G_{es}$ $mC_{eo}$ $mC_{eo}$ $A_{eo}$ $G_{eo}$ $G_{ds}$ $mC_{ds}$ $T_{ds}$ $G_{ds}$ $G_{ds}$ $T_{ds}$ $T_{ds}$ $A_{ds}$ $T_{ds}$ $G_{ds}$ $A_{eo}$ $mC_{eo}$ $T_{es}$ $mC_{es}$ $A_e$ | 18 | 29 | 22 | 21 | 92 | 51 | 1 |
| | 719234 | Chol-TEG-$U_{ms}$ $G_{ms}$ $A_{ro}$ $G_{ro}$ $U_{ro}$ $C_{ro}$ $A_{ro}$ $U_{ro}$ $A_{ro}$ $A_{ro}$ $C_{ro}$ $C_{ro}$ $A_{ro}$ $G_{ro}$ $C_{ro}$ $C_{ro}$ $U_{ro}$ $G_{rs}$ $G_{ms}$ $C_m$ | | | | | | | 2 |

Subscripts in the table above: "s" represents a phosphorothioate internucleoside linkage, "o" represents a phosphate internucleoside linkage, "d" represents a 2'-deoxynucleoside, "e" represents a 2'-MOE modified nucleoside, "r" represents a 2'-ribonucleoside (2'-hydroxy), "m" represents 2'-O-methyl modified nucleoside. Superscripts: "m" before a C represents a 5-methylcysteine. The structures of "Chol-TEG-", "Toco-TEG-", "C10-TEG-", and "C16-TEG-" are shown below.

Chol-TEG-:

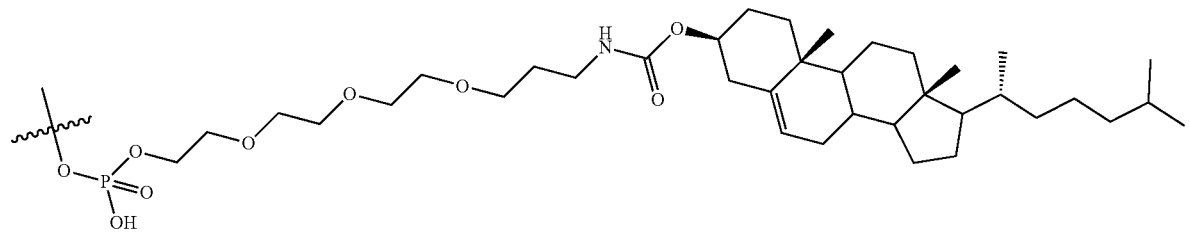

Toco-TEG-:

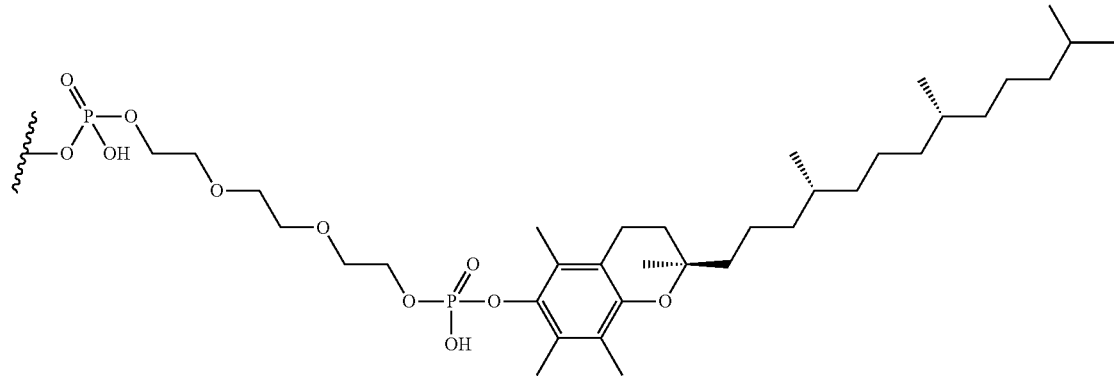

C10-TEG- and C16-TEG-:

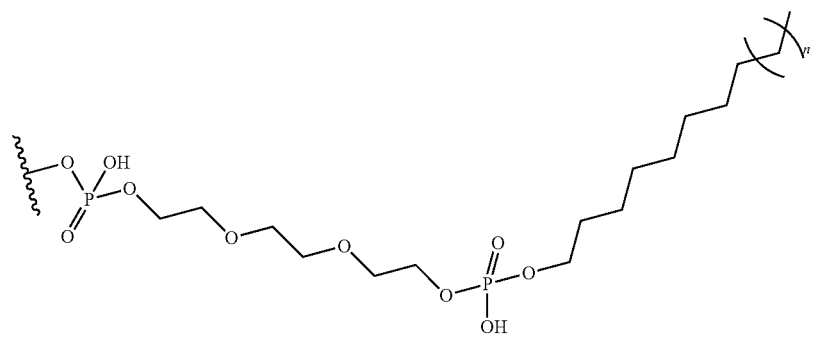

wherein n is 1 in "C10-TEG-", and n is 7 in "C16-TEG-".

Example 2: Effects of Duplexes Comprising a Lipophilic Conjugate Group In Vivo Duplexes, each consisting of two oligomeric compounds, are described in the table below. One oligomeric compound of each duplex comprises an antisense oligonucleotide (Isis No. 626112 or Isis No. 556089) that is complementary to both human and mouse MALAT-1 transcripts. The other oligomeric compound of each duplex comprises an oligonucleotide and a lipophilic conjugate group. The effects of the duplexes on MALAT-1 expression were tested in vivo. Wild type C57bl/6 mice each received an intravenous injection, via the tail vein, of a duplex listed in the table below, Isis No. 626112 alone, Isis No. 556089 alone, or saline. The dosages listed in the table below indicate the amount of Isis No. 626112 or Isis No. 556089 that was administered in each injection. Each treatment group consisted of three or four mice. Three days after the injection, the animals were sacrificed. MALAT-1 RNA expression was analyzed in heart, macrophages (Macs), trigeminal ganglia (TG), sciatic nerve (SN), and dorsal root ganglion (DRG) by RT-qPCR and normalized to total RNA using RiboGreen (Thermo Fisher Scientific, Carlsbad, Calif.). The average results for each group are shown below as the percent normalized MALAT-1 RNA levels relative to average results for the vehicle treated animals.

TABLE 2

MALAT-1 expression in vivo

| Duplex | Isis No. | Sequence (5' to 3') | Dosage (μmol/kg) | Heart | Macs | TG | SN | DRG | SEQ ID NO. |
|---|---|---|---|---|---|---|---|---|---|
| n/a | 626112 | $G_{es}$ $^mC_{eo}$ $^mC_{eo}$ $A_{eo}$ $G_{eo}$ $G_{ds}$ $^mC_{ds}$ $T_{ds}$ $G_{ds}$ $G_{ds}$ $T_{ds}$ $T_{ds}$ $A_{ds}$ $T_{ds}$ $G_{ds}$ $A_{eo}$ $^mC_{eo}$ $T_{es}$ $^mC_{es}$ $A_e$ | 14 | 48 | 69 | 45 | 67 | 79 | 1 |
| 4 | 626112 | See above | 14 | 17 | 16 | 32 | 31 | 44 | 1 |
|  | 719234 | Chol-TEG-$U_{ms}$ $G_{ms}$ $A_{ro}$ $G_{ro}$ $U_{ro}$ $C_{ro}$ $A_{ro}$ $U_{ro}$ $A_{ro}$ $A_{ro}$ $C_{ro}$ $C_{ro}$ $A_{ro}$ $G_{ro}$ $C_{ro}$ $C_{ro}$ $U_{ro}$ $G_{rs}$ $G_{ms}$ $C_m$ |  |  |  |  |  |  | 2 |
| n/a | 556089 | $G_{ks}$ $^mC_{ks}$ $A_{ks}$ $T_{ds}$ $T_{ds}$ $^mC_{ds}$ $T_{ds}$ $A_{ds}$ $A_{ds}$ $T_{ds}$ $A_{ds}$ $G_{ds}$ $^mC_{ds}$ $A_{ks}$ $G_{ks}$ $^mC_k$ | 4.5 | 67 | 48 | 79 | 77 | 88 | 3 |

TABLE 2-continued

MALAT-1 expression in vivo

| Duplex | Isis No. | Sequence (5' to 3') | Dosage (µmol/kg) | Heart | Macs | TG | SN | DRG | SEQ ID NO. |
|---|---|---|---|---|---|---|---|---|---|
| 5 | 556089 | See above | 4.5 | 67 | 40 | 51 | 64 | 59 | 3 |
|   | 827936 | Toco-TEG-$G_{es}$ $^mC_{es}$ $T_{eo}$ $G_{do}$ $^mC_{do}$ $T_{do}$ $A_{do}$ $T_{do}$ $T_{do}$ $A_{do}$ $G_{do}$ $A_{do}$ $A_{do}$ $T_{es}$ $G_{es}$ $^mC_e$ |   |   |   |   |   |   | 4 |
| 6 | 556089 | See above | 4.5 | 56 | 53 | 64 | 81 | 41 | 3 |
|   | 827937 | Toco-$G_{ms}$ $C_{ms}$ $U_{ro}$ $G_{ro}$ $C_{ro}$ $U_{ro}$ $A_{ro}$ $U_{ro}$ $U_{ro}$ $A_{ro}$ $G_{ro}$ $A_{ro}$ $A_{ro}$ $U_{rs}$ $G_{ms}$ $C_m$ |   |   |   |   |   |   | 5 |

See legend for Table 1 for subscripts and superscript key. Subscript "k" represents a cEt modified bicyclic sugar moiety. The structures of "Chol-TEG-" and "Toco-TEG-", are shown in Example 1. The structure of "Toco-" is:

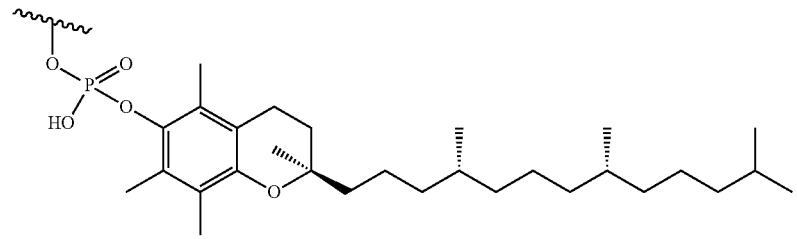

Example 3: Effects of Duplexes Comprising a Lipophilic Conjugate Group In Vivo A duplex, consisting of two oligomeric compounds, is described in the table below. One oligomeric compound of the duplex comprises an antisense oligonucleotide (Isis No. 486178) that is complementary to both human and mouse dystrophia myotonica-protein kinase (DMPK) transcripts. The other oligomeric compound of the duplex comprises an oligonucleotide and a lipophilic conjugate group. The effects of the duplex on DMPK expression were tested in vivo. Wild type Balb-C mice each received an intravenous injection of the duplex listed in the table below, Isis No. 486178 alone, or saline once per week for four weeks. The dosages listed in the table below indicate the amount of Isis No. 486178 that was administered in each injection. Each treatment group consisted of three or four mice. Seven days after the final injection, the animals were sacrificed. DMPK mRNA expression was analyzed in liver, diaphragm (Dia), quadriceps (Quad), tibialis anterior (TA), heart, and gastrocnemius (Gast) using RT-qPCR and normalized to total RNA using RiboGreen (Thermo Fisher Scientific, Carlsbad, Calif.). The average results for each group are shown below as the percent normalized DMPK RNA levels relative to average results for the vehicle treated animals.

TABLE 3

DMPK expression in vivo

| Isis No. | Sequence (5' to 3') | Duplex | Dosage (mg/kg) | Liver | Dia | Quad | TA | Heart | Gast | SEQ ID NO. |
|---|---|---|---|---|---|---|---|---|---|---|
| 486178 | $A_{ks}$ $^mC_{ks}$ $A_{ks}$ $A_{ds}$ $T_{ds}$ $A_{ds}$ $A_{ds}$ $A_{ds}$ $T_{ds}$ $A_{ds}$ $^mC_{ds}$ $^mC_{ds}$ $G_{ds}$ $A_{ks}$ $G_{ks}$ $G_k$ | n/a | 25 | 8 | 41 | 32 | 26 | 55 | 32 | 6 |
|   |   |   | 50 | 6 | 30 | 13 | 21 | 21 | 18 |   |
| 486178 | See above | 7 | 25 | 5 | 27 | 8 | 15 | 22 | 18 | 6 |
| 694790 | Toco-$C_{ms}$ $C_{ms}$ $U_{ro}$ $C_{ro}$ $G_{ro}$ $G_{ro}$ $U_{ro}$ $A_{ro}$ $U_{ro}$ $U_{ro}$ $U_{ro}$ $A_{ro}$ $U_{ro}$ $U_{rs}$ $G_{ms}$ $U_m$ |   | 50 | 5 | 14 | 8 | 16 | 10 | 13 | 7 |

See legends of Table 1 and 2 for subscripts and superscripts key. The structure of "Toco-" is shown in Example 2.

Example 4: Effects of Duplexes Comprising a Lipophilic Conjugate Group In Vivo Duplexes, consisting of two oligomeric compounds, are described in the table below. One oligomeric compound of each duplex comprises an antisense oligonucleotide (Isis No. 440762) that is complementary to mouse SCARB1 scavenger receptor class B, member 1 (SRB-1) transcript. The other oligomeric compound of the duplex comprises an oligonucleotide and a lipophilic conjugate group. The effects of the duplex on SRB-1 expression were tested in vivo. Wild type mice each received an intravenous injection of a duplex listed in the table below, Isis No. 440762 alone, or saline once per. The dosages listed in the table below indicate the amount of Isis No. 440762 that was administered in each injection. Each treatment group consisted of three or four mice. After the final injection, the animals were sacrificed. SRB-1 mRNA expression was analyzed in liver using RT-qPCR and normalized to total RNA using RiboGreen (Thermo Fisher Scientific, Carlsbad, Calif.). The average results for each group are shown below as the percent normalized SRB-1 RNA levels relative to average results for the vehicle treated animals.

TABLE 4

SRB-1 expression in vivo

| Isis No. | Sequence (5' to 3') | Duplex | Dosage (mg/kg) | SRB-1 mRNA level (% Vehicle) | SEQ ID NO. |
|---|---|---|---|---|---|
| 440762 | $T_{ks}\ ^mC_{ks}\ A_{ds}\ G_{ds}\ T_{ds}\ ^mC_{ds}\ A_{ds}\ T_{ds}\ G_{ds}\ A_{ds}\ ^mC_{ds}\ T_{ds}\ T_{ks}\ ^mC_k$ | n/a | 3 | 51 | 8 |
| 440762 655462 | See above  Toco-$G_{ms}\ A_{ms}\ A_{ro}\ G_{ro}\ U_{ro}\ C_{ro}\ A_{ro}\ U_{ro}\ G_{ro}\ A_{ro}\ C_{ro}\ U_{rs}\ G_{ms}\ A_m$ | 8 | 1 | 33 | 8 9 |
| 440762 663429 | See above  Toco-$G_{eo}\ A_{eo}\ A_{do}\ G_{do}\ T_{eo}\ ^mC_{do}\ A_{eo}\ T_{do}\ G_{eo}\ A_{do}\ ^mC_{eo}\ T_{do}\ G_{eo}\ A_e$ | 9 | 1 | 50 | 8 10 |
| 440762 663430 | See above  Toco-$G_{es}\ A_{es}\ A_{do}\ G_{do}\ T_{eo}\ ^mC_{do}\ A_{eo}\ T_{do}\ G_{eo}\ A_{do}\ ^mC_{eo}\ T_{ds}\ G_{es}\ A_e$ | 10 | 1 | 51 | 8 10 |
| 440762 663752 | See above  Toco-$G_{fs}\ A_{fs}\ A_{fo}\ G_{fo}\ U_{fo}\ C_{fo}\ A_{fo}\ U_{fo}\ G_{fo}\ A_{fo}\ C_{fo}\ U_{fs}\ G_{fs}\ A_f$ | 11 | 1 | 97 | 8 9 |
| 440762 671663 | See above  Toco-$G_{ms}\ A_{ms}\ A_{ro}\ G_{fo}\ U_{ro}\ C_{ro}\ A_{fo}\ U_{ro}\ G_{ro}\ A_{fo}\ C_{ro}\ U_{rs}\ G_{ms}\ A_m$ | 12 | 1 | 34 | 8 9 |
| 440762 671221 | See above  Toco-$G_{ks}\ A_{ks}\ A_{ro}\ G_{ro}\ U_{ro}\ C_{ro}\ A_{ro}\ U_{ro}\ G_{ro}\ A_{ro}\ C_{ro}\ U_{rs}\ G_{ks}\ A_k$ | 13 | 1 | 30 | 8 9 |
| 440762 674021 | See above  Toco-$G_{ms}\ A_{ms}\ A_{do}\ G_{do}\ T_{do}\ C_{do}\ A_{do}\ T_{do}\ G_{do}\ A_{do}\ C_{do}\ T_{ds}\ G_{ms}\ A_m$ | 14 | 1 | 44 | 8 10 |
| 440762 675421 | See above  Toco-$G_{es}\ A_{es}\ A_{ro}\ G_{ro}\ U_{ro}\ C_{ro}\ A_{ro}\ U_{ro}\ G_{ro}\ A_{ro}\ C_{ro}\ U_{rs}\ G_{es}\ A_e$ | 15 | 1 | 36 | 8 9 |

See legends of Table 1 and 2 for subscripts and superscripts key. Subscript "f" indicates a 2'-fluoro modification. The structure of "Toco-" is shown in Example 2.

The invention claimed is:

1. A method of reducing the expression of DMPK in skeletal muscle and cardiac muscle, comprising administering to a subject a duplex comprising a first oligomeric compound and a second oligomeric compound wherein the first oligomeric compound comprises a first modified oligonucleotide consisting of 10-30 linked nucleosides; and the second oligomeric compound comprises a second modified oligonucleotide consisting of 10-30 linked nucleosides and a conjugate group;

wherein the conjugate group comprises a conjugate moiety and a conjugate linker, wherein the conjugate moiety is cholesterol; and wherein the conjugate linker comprises at least one cleavable moiety; and wherein the nucleobase sequence of the first oligomeric compound is complementary to the nucleobase sequence of the second oligomeric compound and to a DMPK mRNA.

2. The method of claim 1, wherein the first modified oligonucleotide comprises at least one modified nucleoside.

3. The method of claim 2, wherein the first modified oligonucleotide comprises a least one modified nucleoside comprising a modified sugar moiety.

4. The method of claim 3, wherein the first modified oligonucleotide comprises at least one modified nucleoside comprising a bicyclic sugar moiety.

5. The method of claim 4, wherein the first modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

6. The method of claim 2, wherein the first modified oligonucleotide comprises at least one modified nucleoside comprising a modified non-bicyclic sugar moiety.

7. The method of claim 6, wherein the first modified oligonucleotide comprises at least one modified nucleoside comprising a non-bicyclic sugar moiety comprising a 2'-MOE or 2'-O-Methyl modified sugar moiety.

8. A method of reducing the expression of DMPK in skeletal muscle and cardiac muscle, comprising administering to a subject a duplex comprising a first oligomeric compound and a second oligomeric compound wherein the first oligomeric compound comprises a first modified oligonucleotide consisting of 10-30 linked nucleosides; and the second oligomeric compound comprises a second modified oligonucleotide consisting of 10-30 linked nucleosides and a conjugate group;

wherein the conjugate group comprises a conjugate moiety and a conjugate linker, wherein the conjugate moiety is tocopherol; and wherein the conjugate linker comprises at least one cleavable moiety; and wherein the nucleobase sequence of the first oligomeric compound is complementary to the nucleobase sequence of the second oligomeric compound and to a DMPK mRNA.

9. The method of claim 8, wherein the first modified oligonucleotide comprises at least one modified nucleoside.

10. The method of claim 9, wherein the first modified oligonucleotide comprises a least one modified nucleoside comprising a modified sugar moiety.

11. The method of claim 10, wherein the first modified oligonucleotide comprises at least one modified nucleoside comprising a bicyclic sugar moiety.

12. The method of claim 11, wherein the first modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

13. The method of claim 9, wherein the first modified oligonucleotide comprises at least one modified nucleoside comprising a modified non-bicyclic sugar moiety.

14. The method of claim 13, wherein the first modified oligonucleotide comprises at least one modified nucleoside comprising a non-bicyclic sugar moiety comprising a 2'-MOE or 2'-O-Methyl modified sugar moiety.

15. The method of claim 1, wherein the first modified oligonucleotide has a sugar motif consisting of:

a 5'-region consisting of 1-5 linked 5'-nucleosides;

a central region consisting of 6-10 linked central region nucleosides; and a 3'-region consisting of 1-5 linked 3'-region nucleosides; wherein each of the 5'-region nucleosides and each of the 3'-region comprises a modified sugar moiety.

16. The method of claim 8, wherein the first modified oligonucleotide has a sugar motif consisting of:
- a 5'-region consisting of 1-5 linked 5'-nucleosides;
- a central region consisting of 6-10 linked central region nucleosides; and
- a 3'-region consisting of 1-5 linked 3'-region nucleosides; wherein
- each of the 5'-region nucleosides and each of the 3'-region comprises a modified sugar moiety.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
gccaggctgg ttatgactca					20

<210> SEQ ID NO 2
<211> LENGTH: 23
<212> TYPE: DNA

```
<213> ORGANISM: Artificial sequence
<220> FEATURE:
<223> OTHER INFORMATION: Synthetic oligonucleotide

<400> SEQUENCE: 2
tcagccaggc tggttatgac tca                                              23

<210> SEQ ID NO 3
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 3
gcattctaat agcagc                                                      16

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
tcagcattct aatagcagc                                                   19

<210> SEQ ID NO 5
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 5
aggatatgga accaaa                                                      16

<210> SEQ ID NO 6
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 6
tcaaggatat ggaaccaaa                                                   19

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
gacaacttgg agcttg                                                      16

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8
tcagacaact tggagcttg                                                   19
```

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
ctggtatgag gcctga                                                     16

<210> SEQ ID NO 10
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 10
tcactggtat gaggcctga                                                  19

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
acaataaata ccgagg                                                     16

<210> SEQ ID NO 12
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 12
tcaacaataa ataccgagg                                                  19

<210> SEQ ID NO 13
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(8)
<223> OTHER INFORMATION: bases at these positions are RNA
<220> FEATURE:
<221> NAME/KEY: misc_feature
<222> LOCATION: (10)..(14)
<223> OTHER INFORMATION: bases at these positions are RNA

<400> SEQUENCE: 13
cutagcactg gccu                                                       14

<210> SEQ ID NO 14
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 14
agcatagtta acgagctccc                                               20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
aatggtttat tccatggcca                                               20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
gcagccatgg tgatcaggag                                               20

<210> SEQ ID NO 17
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 17
ggttcccgag gtgccca                                                  17

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gcacactcag caggaccccc                                               20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ccacctttgg gtgaatagca                                               20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
tgccatttaa tgagcttcac                                               20

```
<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
tcccgaatgt ccgaca                                                    16

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
atcccacgcc cctgtccagc                                                20
```